(12) United States Patent
Weber et al.

(10) Patent No.: US 7,070,613 B2
(45) Date of Patent: Jul. 4, 2006

(54) NON-COMPLIANT BALLOON WITH COMPLIANT TOP-LAYER TO PROTECT COATED STENTS DURING EXPANSION

(75) Inventors: Jan Weber, Maple Grove, MN (US); Tim O'Connor, Claregalway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/035,158

(22) Filed: Jan. 4, 2002

(65) Prior Publication Data
US 2003/0130716 A1 Jul. 10, 2003

(51) Int. Cl.
*A61F 2/06* (2006.01)
*A61M 29/00* (2006.01)

(52) U.S. Cl. ...................... 623/1.11; 606/192
(58) Field of Classification Search ............... 623/1.15, 623/1.11, 1.42, 1.46; 606/192, 193, 194, 606/191, 198, 108
See application file for complete search history.

(56) References Cited

U.S. PATENT DOCUMENTS

| 4,950,227 | A | * | 8/1990 | Savin et al. | 623/1.12 |
| 5,116,318 | A | * | 5/1992 | Hillstead | 604/103.14 |
| 5,409,495 | A | * | 4/1995 | Osborn | 623/1.11 |
| 5,843,089 | A | * | 12/1998 | Sahatjian et al. | 623/1.11 |
| 6,544,222 | B1 | * | 4/2003 | Yang | 604/103.01 |
| 6,660,034 | B1 | * | 12/2003 | Mandrusov et al. | 623/1.42 |
| 6,852,116 | B1 | * | 2/2005 | Leonhardt et al. | 606/108 |

* cited by examiner

*Primary Examiner*—Alvin J. Stewart
(74) *Attorney, Agent, or Firm*—Kenyon & Kenyon LLP

(57) ABSTRACT

In order to minimize the potential for damage to biocompatible and/or therapeutic-containing stent coatings, there is provided a compliant elastic sheath over layer between a non-compliant stent expansion balloon and an unexpanded stent, which is secured over the balloon with a securing crimp. This stent deployment assembly, which is mounted on a catheter, is maneuvered through a patient's body to a desired deployment site and then inflated to expand the stent to the desired diameter. During expansion, the compliant elastic material between the stent and the non-compliant balloon prevents non-compliant balloon-induced damage to the stent's coating, as well as preventing degradation of the non-compliant balloon by, for example, stent-caused punctures. The deflated non-compliant stent expansion balloon and compliant elastic sheath are then withdrawn from the patient's body, leaving the deployed stent at the desired implantation site with its coating substantially intact.

19 Claims, 2 Drawing Sheets

NON-COMPLIANT BALLOON WITH COMPLIANT TOP-LAYER TO PROTECT COATED STENTS DURING EXPANSION

FIELD OF THE INVENTION

The present invention generally regards providing protection for a coated stent during its handling and use. More specifically, the present invention regards providing a compliant protective layer between a stent coated with a polymer and/or a therapeutic substance, and a non-compliant inflatable balloon used to expand the stent into a desired configuration in order to protect the stent coating from degradation during deployment.

BACKGROUND

The positioning and deployment of medical implants is a common often-repeated procedure of modern medicine. Medical implants may be used for innumerable medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects.

Such localized delivery of therapeutic agents has been proposed or achieved using medical devices such as catheters, needle devices and various coated implantable devices such as stents. These implants may be delivered by securing them to the distal end of a delivery device, positioning the distal end of the device near a target delivery site, and then deploying the implant from the device to its desired position. The implant may be deployed by inflating the distal end of the device or through other forces that urge the implant from the device's distal end. When the implant has been coated this coating is susceptible to being damaged or completely removed from the implant during the deployment process— an unwanted result.

The mechanical process of deploying the implant often exerts significant shearing and adhesion forces on and against the surface of the coating of the implant. These forces can strip, damage or otherwise deplete the amount of coating on the implant. When the amount of coating is depleted the implant's effectiveness may be compromised and additional risks may be inured into the procedure. For example, when the coating of the implant includes a therapeutic, if some of the coating were removed during deployment, the therapeutic may no longer be able to be administered to the target site in a uniform and homogenous manner. Thus, some areas of the target site may receive high quantities of therapeutic while others may receive low quantities of therapeutic. Similarly, if the therapeutic is ripped from the implant it can reduce or slow down the blood flowing past it, thereby, increasing the threat of thrombosis or, if it becomes dislodged, the risk of embolisms.

The delivery of expandable stents is a specific example of a medical procedure that involves the deployment of coated implants. Expandable stents are tube-like medical devices, typically made from stainless steel, Tantalum, Platinum or Nitinol alloys, designed to support the inner walls of a lumen within the body of a patient. These stents are typically positioned within a lumen of the body and, then expanded to provide internal support for the lumen. They may be self-expanding or, alternatively, may require external forces to expand them, such as by an inflating a balloon within the stent's inner diameter. In either case they are typically deployed through the use of a catheter of some kind. These catheters will typically carry the stent at their distal end.

Because of the direct contact of the stent with the inner walls of the lumen, stents have been coated with various compounds and therapeutics to enhance their effectiveness. These coatings may, among other things, be designed to facilitate the acceptance of the stent into its applied surroundings. Such coatings may also be designed to facilitate the delivery of a therapeutic to the target site for treating, preventing, or otherwise affecting the course of a disease or tissue or organ dysfunction.

The term "therapeutic agent" as used herein includes one or more "therapeutic agents" or "drugs". The terms "therapeutic agents" and "drugs" are used interchangeably herein and include pharmaceutically active compounds, nucleic acids with and without carrier vectors such as lipids, compacting agents (such as histones), virus (such as adenovirus, andenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anticoagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

When a polymer and/or therapeutic coating is haphazardly applied or has somehow been removed during the stent's manufacture or delivery, the stent's effectiveness can be compromised. In certain circumstances faulty or ineffectively deployed stents can require the removal and reinsertion of the stent through a second medical procedure. For example, as the balloon at the distal end of the stent is inflated, to expand and position the stent, frictional shear forces are created between the surface of the catheter and the stent coating. These frictional surface shear forces, as well as the adhesion forces between the coating and the stent, act to tear away or unevenly redistribute the stent coating. Thus, the physical forces used to deliver the stent can create an abating result that reduces the overall effectiveness of a deployed coated stent.

During manufacture of assemblies of non-self-expanding stents and expansion balloons over the distal end of a catheter, the stent may be placed over the outer diameter of the unexpanded balloon and crimped onto the balloon. Frequently, the stent expansion balloon is composed of a non-compliant material, such as Polyimide, PET, HDPE or Pebax. Further, in order to minimize the profile of the stent assembly, it is common practice to form a number of wings in the wall of the non-compliant balloon and fold the wings down along the side of the balloon prior to crimping the stent over the balloon. The folding of wings in the non-compliant balloon minimizes the diameter of the uninflated balloon, and hence the diameter of the final crimped-on stent assembly. Moreover, when the stent expansion balloon is composed of a non-compliant material, the diameter of the expanded balloon, and therefore also the expanded stent, is more or less independent of the balloon inner pressure.

There are some disadvantages associated with the use of non-compliant balloons in stent assemblies, both during manufacture of the assembly and during inflation of the balloon and expansion of the stent. For example, during manufacture the hardness of the non-compliant balloon may increase the difficulty in securing the stent over the balloon, such that often high crimping forces must be applied in order to adequately secure the stent to the non-compliant balloon. These high securement forces increase the risk for stent-caused punctures. Likewise, during expansion of the stent during implantation, the wings of the non-compliant balloon move relative to the stent in a tangential direction. If the stent being implanted has a coating on its surface, the non-compliant balloon's sliding tangential motion may abrade or otherwise damage the stent coating.

Alternatively, a compliant balloon (i.e., a balloon composed of well-known elastic materials, such as Latex or silicone rubber) may be used for expanding a stent. Compliant balloons are softer than non-compliant balloons, and thus permit the stent to obtain a better "grip" on the balloon, which in turn permits the stent to be more easily secured to the stent using lower crimping forces. In addition, compliant balloons need not be formed and folded into a preferred pre-expansion shape like non-compliant balloons, as compliant balloons already have a minimal diameter in their unexpanded state. Compliant balloons also expand principally in the radial direction, hence there is no tangential sliding motion relative to the expanding stent, which in turn may reduce the chances of probability of stent coating damage during stent expansion.

Compliant balloons have their own disadvantages, however. For example, the expanded diameter of a compliant balloon depends directly on the applied pressure, requiring exacting control of inflation pressures to ensure a stent is properly expanded. In addition, compliant balloons sometimes exhibit what is sometimes referred to as a "dog-bone effect" during expansion, wherein the portions of the balloon outside the length of the stent expand more that the portion of the balloon within the length of the stent. Accordingly, use of compliant balloons to inflate non-self-expanding stents may not be preferred in some applications.

SUMMARY OF THE INVENTION

The present invention is directed to an apparatus and method for overcoming the foregoing disadvantages. Specifically, there is provided a stent-expansion balloon made of a non-compliant material, over which a compliant elastic layer in the form of a sheath or tube or coating is placed and an expandable stent is crimped thereover. The use of a compliant sheath permits the securing crimp to be made with lower crimping forces, thereby decreasing the potential for stent-manufacture-induced damage to a coating on the stent.

The stent deployment assembly, which is mounted on the distal end of a catheter, is maneuvered through the body of a patient to a desired implantation location. The non-compliant stent expansion balloon is then inflated to expand the stent to the desired diameter. During expansion, the compliant elastic material between the stent and the non-compliant balloon prevents non-compliant balloon-induced damage to the stent's coating, as well as degradation of the non-compliant balloon by, for example, stent-caused punctures. The non-compliant stent expansion balloon is then deflated to disengage the non-compliant balloon and the compliant elastic sheath from the stent. Once deflated, the catheter with the deflated non-compliant balloon and the compliant elastic sheath may be withdrawn from the patient's body, leaving the expanded stent at the desired implantation site within the patient's body with a substantially intact coating.

In one embodiment of the invention, manufacture of the stent deployment assembly is conducted by placing a non-compliant balloon, in its unexpanded condition, i.e., with folded wings, within a sheath made of a compliant elastic material that is held open by a purpose-built expansion fixture. Once the non-compliant balloon is placed inside the compliant elastic sheath, the sheath is allowed to contract and conform to the outer surface of the unexpanded non-compliant balloon. This balloon sub-assembly is then placed within an unexpanded, coated stent of predetermined diameter, which is then secured to the balloon subassembly by crimping the stent on top of the compliant elastic sheath. The use of a compliant elastic layer between the stiff metal stent and the non-compliant stent expansion balloon permits the stent to be satisfactorily secured over the expansion balloon without use of high crimping forces.

DETAILED DESCRIPTION

Figure 1:
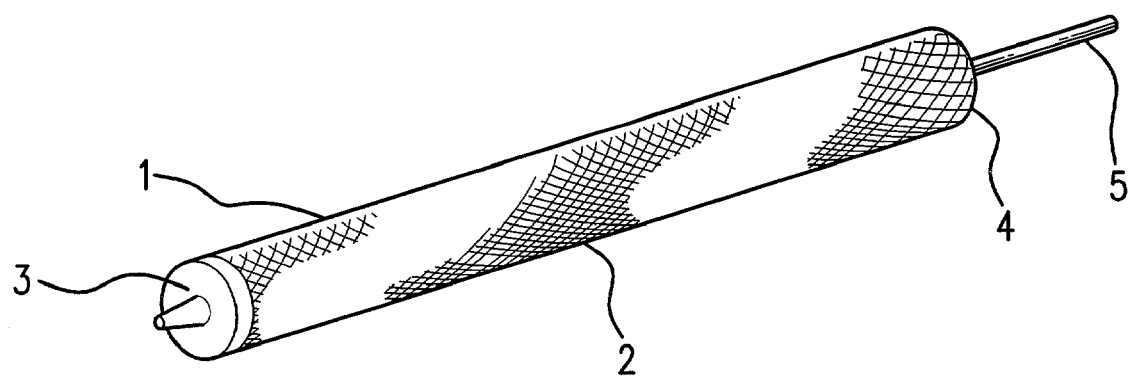
FIG. 1 is an oblique view of one embodiment of a stent assembly in accordance with the present invention.

FIG. 1 illustrates an embodiment of the present invention, prior to stent expansion within the body of a patient. The stent deployment assembly 1 shown in FIG. 1 may comprise: a non-self-expanding stent 2 of well-known material such as stainless steel, Tantalum, Platinum of Nitinol alloys and coated with at least one of a protective material, a therapeutic, or a therapeutic-bearing material; a compliant sheath 3 of well-known elastic material, such as Latex or silicone rubber; and a non-compliant stent expansion balloon 4 in a folded configuration within compliant elastic sheath 3. Stent expansion balloon 4 may be made from one of a number of well-known, relatively stiff polymeric materials, such as polyamide, thermoplastic polyamide, polyesters, polyphenylene sulfides, and polyethylene terephthalate ("PET"), and may be attached to the distal end of a catheter 5 though its center in a conventional manner.

Figure 2:
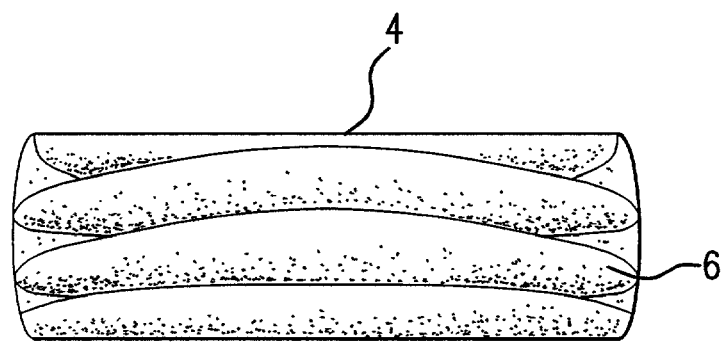
FIG. 2 is an oblique view of a non-compliant stent-expansion balloon in its uninflated state in accordance with an alternative embodiment of the present invention.

As shown in FIG. 2, in the present embodiment the non-compliant stent expansion balloon 4 is prepared for use in the stent assembly by folding the uninflated balloon such that the balloon wall forms longitudinal wings 6 which wrap around the longitudinal axis of the non-compliant balloon. The folded stent expansion balloon 4 is thus formed into a generally cylindrical shape. Another embodiment of folding the non-compliant balloon into a cylindrical shape with minimal profile is to form so-called T-wings. These wings have the shape of a T in cross-section and unfold without sliding tangentially underneath the stent. The crimp forces required, however, are still high.

The following describes the method of use of the above-described stent deployment assembly. During a procedure for insertion and placement of a stent in the body of a patient, stent deployment assembly 1, mounted on the distal end of catheter 5, is maneuvered to the desired emplacement location by conventional means. At the desired stent emplacement site, non-compliant stent expansion balloon 4 is inflated via fluid pressure supplied through catheter 5. As non-compliant balloon 4 begins to inflate, its folded wings 6 begin to unfold, expanding the balloon's diameter in the radial direction. This radial expansion is accompanied by tangential movement of the outer edges of the balloon wings, which slide across the inner surface of compliant elastic sheath 3. Because compliant elastic sheath 3 separates the edges of balloon wings 6 from the inner surface of stent 2, the protective or therapeutic coating on the surfaces of stent 2 is not disturbed by the unfolding balloon wings, and any sharp edges on stent 2 are precluded from causing holes and leaks in non-compliant balloon 4. Once stent 2 had been fully expanded to the desired diameter, the pressure within non-compliant stent expansion balloon 4 is decreased, allowing balloon 4 to contract, aided by pressure applied by contracting compliant elastic sheath 3. Once sheath 3 is contracted sufficiently to disengage from the inner surface of stent 2, the catheter to which non-compliant stent expansion balloon 4 is mounted may be withdrawn from the patient's body without damaging the coating on stent 2.

Figure 3:
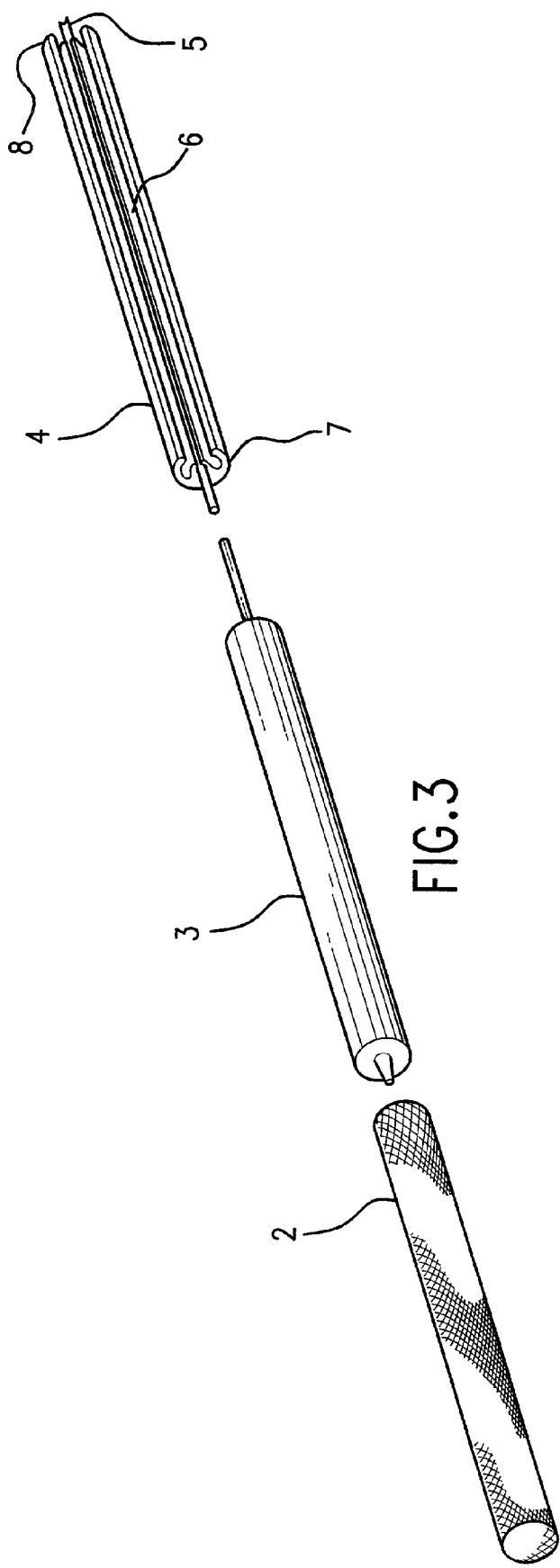
FIG. 3 is an exploded view of the stent assembly illustrated in FIG. 1, showing the components of the stent assembly.

FIG. 3 is an exploded view of the principal components of the present embodiment of the stent deployment assembly. The folded non-compliant balloon 4 is inserted into compliant elastic sheath 3 to form a balloon subassembly. In order to facilitate the insertion of non-compliant stent expansion balloon 4 into compliant elastic sheath 3, compliant elastic sheath 3 is expanded, for example by inflation within a purpose-built fixture, or by mechanical means such as arms inserted into the sheath and moved radially outward. Following insertion of non-compliant stent expansion balloon 4 into compliant elastic sheath 3, the sheath is permitted to contract to conform to the outer surface of non-compliant stent expansion balloon 4.

After non-compliant stent expansion balloon 4 and compliant elastic sheath 3 are formed into a balloon subassembly, stent 2 is placed over the subassembly and sufficient crimping forces are applied to secure stent 2 over compliant elastic sheath 3 to preclude longitudinal movement of stent 2 relative to compliant elastic sheath 3. The crimping forces may be applied along the entire length of stent 2, or alternatively at distal end 7 or proximal end 8 of non-compliant balloon 4, or at any combination of these locations. It is preferable that compliant elastic sheath 3 be relatively transparent to permit radio opaque markings on non-compliant balloon 4 (not shown) to be seen in order to permit correct positioning of stent 2 prior to crimping over the compliant elastic sheath 3. Due to the improved resistance to stent longitudinal motion provided by the compliant elastic layer (as compared to crimping the stent directly over the non-compliant balloon), the usual measures to minimize longitudinal motion such as hubs (polymer rings) or spiral inner sheaths can be left out of the stent assembly. Accordingly, because the usual measures are left out, the overall profile (diameter) of the unexpanded stent assembly need not be any larger than a usual non-compliant balloon-inflated stent deployment assembly.

Figure 4:
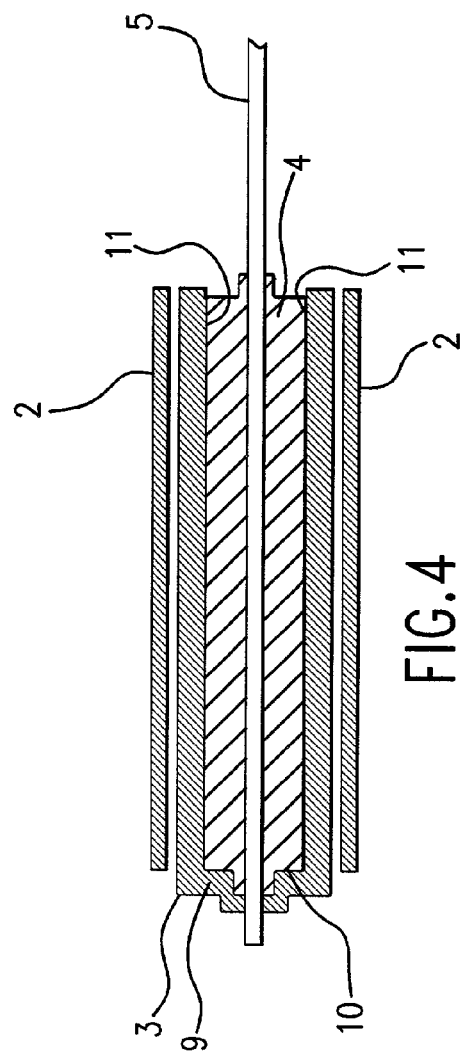
FIG. 4 is a cross-section view of the stent assembly illustrated in FIG. 1 along the longitudinal axis of the stent assembly, showing the arrangement of the stent assembly components

FIG. 4 provides a cross-section view of the foregoing embodiment. In this figure, non-compliant balloon 4 is shown after insertion into compliant elastic sheath 3, and compliant elastic sheath 3 is shown with a closed end 9 over distal end 7 of balloon 4. Alternatively, compliant elastic sheath 3 may be an open-ended tube, or may be closed over the proximal only or closed over both ends of the non-compliant balloon. FIG. 4 further shows the position of stent 2 relative to the balloon subassembly following crimping of stent 2 onto compliant elastic sheath 3.

In order to ensure compliant elastic sheath 3 remains affixed to non-compliant stent expansion balloon 4, a small amount of adhesive 10 may be applied between the closed end of sheath 3 and balloon 4, preferably at a location outside the area upon which stent 2 is crimped over the balloon subassembly. Alternatively, the adhesive may be placed between sheath 3 and balloon 4 at a location along the length of the balloon subassembly, as long as neither expansion of the balloon nor elasticity of the sheath are compromised. As a further alternative, compliant elastic sheath 3 can be glued to the distal end of catheter 5 and/or to a portion of catheter 5 adjacent to proximal end 8 of non-compliant balloon 4.

Further, as illustrated in FIG. 4, a lubricant 11 such as silicone may be applied between compliant elastic sheath 3 and non-compliant stent expansion balloon 4 along their lengths to permit the balloon's wings to slide more easily in a tangential direction when unfolding beneath sheath 3 during stent expansion. The lubricant improves the ease of stent expansion while minimizing the potential for either tangential movement of compliant elastic sheath 3 relative to the expanding stent (caused by the expanding wings of non-compliant stent expansion balloon 4) or damage to the compliant sheath caused by stent 2.

While the present invention has been described with reference to what are presently considered to be preferred embodiments thereof, it is to be understood that the present invention is not limited to the disclosed embodiments or constructions. On the contrary, the present invention is intended to cover various modifications and equivalent arrangements. In addition, while the various elements of the disclosed invention are described and/or shown in various combinations and configurations, which are exemplary, other combinations and configurations, including more, less or only a single embodiment, are also within the spirit and scope of the present invention.

What is claimed is:

1. An expandable stent deployment assembly for stent implantation within a patient's body, comprising:
   an expandable coated stent with a coating on at least a portion of an inner surface of the stent;
   a stent expansion balloon, expandable from a first configuration to a second configuration, the balloon sized to fit within the expandable stent when the balloon and the stent are unexpanded; and
   a compliant sheath located between the stent expansion balloon and the coated stent, wherein at least some of the coating on the inner surface of the coated stent has not been transferred to the stent from the compliant sheath, and wherein the compliant sheath is transparent.

2. The expandable stent deployment assembly of claim 1, wherein the stent is in contact with the sheath when the stent is unexpanded.

3. The expandable stent deployment assembly of claim 2, wherein the stent is crimped over the sheath.

4. The expandable stent deployment assembly of claim 1, wherein the coating comprises at least one therapeutic agent.

5. The expandable stent deployment assembly of claim 4, wherein the coating comprises one of polyamide, thermoplastic polyamide, polyester, polyphenylene sulfide, and polyethylene terephthalate.

6. The expandable stent deployment assembly of claim 4, wherein the compliant sheath material comprises one of Latex or silicone rubber.

7. The expandable stent deployment assembly of claim 1, wherein the compliant sheath is closed about at least one of a distal end or a proximal end of the stent expansion balloon.

8. The expandable stent deployment assembly of claim 7 wherein the compliant sheath is closed at the distal end and the proximal end of the stent expansion balloon.

9. The expandable stent deployment assembly of claim 1, wherein the compliant sheath comprises a tube, and further wherein the length of the tube is equal to or greater than the length of the stent.

10. The expandable stent deployment assembly of claim 9, further comprising an adhesive located at at least one location between the tube and the stent expansion balloon, wherein an amount and the location of said adhesive are such that movement of the balloon relative to the sheath during stent expansion is not inhibited in a manner that permits a coating on the stent to be damaged.

11. The expandable stent deployment assembly of claim 1, further comprising an adhesive located between the compliant sheath and the stent expansion balloon.

12. The expandable stent deployment assembly of claim 11, further comprising an adhesive located between a distal end of the compliant sheath and the distal end of the stent expansion balloon.

13. The expandable stent deployment assembly of claim 1, further comprising a lubricant located between the compliant sheath and the stent expansion balloon.

14. The expandable stent deployment assembly of claim 1, wherein the coating is in contact with the compliant sheath over the entire length of the stent.

15. The expandable stent deployment assembly of claim 1, wherein the stent is crimped over the compliant sheath over the entire length of the stent.

16. The expandable stent deployment assembly of claim 1, wherein the coating is in contact with the compliant sheath at least one of a distal end and a proximal end of the stent.

17. The expandable stent deployment assembly of claim 1, wherein the stent is crimped over the compliant sheath at at least one of a distal end and a proximal end of the stent.

18. The expandable stent deployment assembly of claim 1, further comprising a lubricant located between the compliant sheath and the stent expansion balloon, the sheath having an outside surface, the outside surface being free of lubricant prior to the expansion of the stent.

19. The expandable stent deployment assembly of claim 1 wherein the stent expansion balloon contains one or more radiopaque markings.

\* \* \* \* \*

UNITED STATES PATENT AND TRADEMARK OFFICE
CERTIFICATE OF CORRECTION

| | | |
|---|---|---|
| PATENT NO. | : 7,070,613 B2 | Page 1 of 2 |
| APPLICATION NO. | : 10/035158 | |
| DATED | : July 4, 2006 | |
| INVENTOR(S) | : Weber et al. | |

It is certified that error appears in the above-identified patent and that said Letters Patent is hereby corrected as shown below:

On the Title Page: item (56),

References Cited:

U.S. PATENT DOCUMENTS insert the following:

| | | | |
|---|---|---|---|
| 5,810,871 | 9/1998 | Tuckey et al.............. | 606/198 |
| 6,174,327 | 1/2001 | Mertens et al............. | 623/1.11 |
| 2001/0049551 | 12/2001 | Tseng et al................ | 623/1.15 |

FOREIGN PATENT DOCUMENTS

| | | | |
|---|---|---|---|
| EP | 0 553 960 | 8/1993 | (EP) |
| WO | 97/09946 | 3/1997 | (WO) |
| EP | 0 872 220 | 10/1998 | (EP) |
| EP | 0 897 730 | 2/1999 | (EP) |
| WO | 99/56663 | 11/1999 | (WO) |

Column 2, line 18, "andenoassociated virus" should be changed to --adeno-associated virus--;
Column 2, line 58, "nitorfurantoin" should be changed to --nitrofurantoin--;
Column 2, line 60, "lisidomine" should be change to --linsidomine--;
Column 2, line 66, "Warafin" should be changed to --warfarin--;
Column 3, lines 1-2, "promotors" should be changed to --promoters--;
Column 3, lines 3-4, "promotors" should be changed to --promoters--;
Column 3, line 12, "endogeneus vasocoactive" should be changed to --endogenous vasoactive--;
Column 3, line 52, "("BMP's")" should be changed to --("BMPs")--;
Column 3, line 55, "BMP's" should be changed to --BMPs--;

UNITED STATES PATENT AND TRADEMARK OFFICE
CERTIFICATE OF CORRECTION

PATENT NO.         : 7,070,613 B2
APPLICATION NO. : 10/035158
DATED               : July 4, 2006
INVENTOR(S)       : Weber et al.

It is certified that error appears in the above-identified patent and that said Letters Patent is hereby corrected as shown below:

Column 4, line 18, "Pebax" should be changed to --PEBAX®
(polyether block amide)--;
Column 4, line 66, "that" should be changed to --than--;
Column 5, line 62, "components" should be changed to --components.--;
Column 6, line 3, "Tantalum, Platinum of Nitinol alloys" should be changed to
--tantalum, platinum, or nitinol alloys--;
Column 6, line 14, "though" should be changed to --through--;
Column 7, line 30, "proximal only" should be changed to --proximal end only--; and
Claim 16, line 3 (column 9, line 1), "sheath at least one" should be changed to
--sheath at at least one--.

Signed and Sealed this

Ninth Day of September, 2008

JON W. DUDAS
*Director of the United States Patent and Trademark Office*